United States Patent
Fenton et al.

(10) Patent No.: US 9,872,680 B2
(45) Date of Patent: Jan. 23, 2018

(54) FILAMENTOUS TISSUE IMPLANT

(71) Applicant: Tissue Solutions, LLC, Marblehead, MA (US)

(72) Inventors: Paul V. Fenton, Marblehead, MA (US); J. Christopher Flaherty, Auburndale, FL (US); Anshuman Shrivastava, Shrivastava (IN)

(73) Assignee: Tissue Solutions, LLC, Marblehead, MA (US)

( * ) Notice: Subject to any disclaimer, the term of this patent is extended or adjusted under 35 U.S.C. 154(b) by 0 days.

(21) Appl. No.: 14/591,147

(22) Filed: Jan. 7, 2015

(65) Prior Publication Data
US 2015/0119907 A1 Apr. 30, 2015

Related U.S. Application Data

(63) Continuation of application No. 13/383,956, filed as application No. PCT/US2010/036190 on May 26, 2010, now Pat. No. 8,956,372.
(Continued)

(51) Int. Cl.
*A61B 17/04* (2006.01)
*A61B 17/06* (2006.01)
(Continued)

(52) U.S. Cl.
CPC .... *A61B 17/06166* (2013.01); *A61B 17/0469* (2013.01); *A61B 17/0482* (2013.01);
(Continued)

(58) Field of Classification Search
CPC ........ A61B 17/06166; A61B 17/06061; A61B 17/0482; A61B 2017/06176;
(Continued)

(56) References Cited

U.S. PATENT DOCUMENTS 2,012,776 A * 8/1935 Roeder ............ A61B 17/12013
606/139
5,037,433 A * 8/1991 Wilk .................. A61B 17/0469
606/139
(Continued)

FOREIGN PATENT DOCUMENTS

SU 549146 3/1977

OTHER PUBLICATIONS

International Search Report and Written Opinion for PCT/US2010/036190, dated Mar. 9, 2011.
(Continued)

*Primary Examiner* — Amy R Weisberg
(74) *Attorney, Agent, or Firm* — Levine Bagade Han LLP

(57) ABSTRACT

A tissue fixation system including a delivery tube and an elongated fastener with a loop at a proximal end and a distal end. A proximal end of an elongated curved needle is attached to the delivery tube. A distal end of the needle is configured to penetrate tissue. The needle includes an open channel sized to receive the elongated fastener with the loop located near the proximal end of the elongated curved needle and the distal end of the elongated fastener located near the distal end of the elongated curved needle. A capture needle is slidably positioned in the delivery tube to slide through the loop in the proximal end of the elongated fastener. The capture needle is configured to grasp the distal end of the elongated fastener and pull the distal end of the elongated fastener through the loop to cinch the elongated fastener.

19 Claims, 13 Drawing Sheets

Related U.S. Application Data

(60) Provisional application No. 61/180,935, filed on May 26, 2009.

(51) Int. Cl.
*A61B 17/00* (2006.01)
*A61B 90/00* (2016.01)

(52) U.S. Cl.
CPC .... *A61B 17/0487* (2013.01); *A61B 17/06061* (2013.01); *A61B 17/0485* (2013.01); *A61B 90/39* (2016.02); *A61B 2017/00867* (2013.01); *A61B 2017/047* (2013.01); *A61B 2017/0472* (2013.01); *A61B 2017/0475* (2013.01); *A61B 2017/0477* (2013.01); *A61B 2017/0619* (2013.01); *A61B 2017/06176* (2013.01); *A61B 2090/037* (2016.02)

(58) Field of Classification Search
CPC ........ A61B 2017/0472; A61B 17/0475; A61B 17/06; A61B 17/0401; A61B 2017/0409; A61B 2017/0427
USPC .................. 606/138–148, 222–227
See application file for complete search history.

(56) References Cited

U.S. PATENT DOCUMENTS

| | | | | |
|---|---|---|---|---|
| 5,089,012 A * | 2/1992 | Prou | ................ | A61B 17/06166 606/224 |
| 5,152,769 A * | 10/1992 | Baber | ................ | A61B 17/0469 112/169 |
| 5,336,231 A * | 8/1994 | Adair | ................ | A61B 17/0469 606/1 |
| 5,540,703 A * | 7/1996 | Barker, Jr. | ............. | A61L 17/04 289/1.2 |
| 5,540,705 A * | 7/1996 | Meade | ............... | A61B 17/0491 606/139 |
| 5,643,295 A * | 7/1997 | Yoon | .................. | A61B 17/0483 606/151 |
| 5,810,849 A * | 9/1998 | Kontos | ............. | A61B 17/0057 606/144 |
| 5,814,052 A * | 9/1998 | Nakao | ............... | A61B 17/12013 606/110 |
| 5,897,564 A * | 4/1999 | Schulze | ............. | A61B 17/0469 112/80.03 |
| 5,968,077 A * | 10/1999 | Wojciechowicz | ............ | 606/228 |
| 6,893,448 B2 * | 5/2005 | O'Quinn | ............ | A61B 17/0469 606/139 |
| 7,235,087 B2 * | 6/2007 | Modesitt | ............ | A61B 17/0057 606/144 |
| 7,285,124 B2 * | 10/2007 | Foerster | ............ | A61B 17/0469 606/139 |
| 7,637,918 B2 * | 12/2009 | Dant | .................. | A61B 17/0469 606/144 |
| 7,875,043 B1 * | 1/2011 | Ashby | ................ | A61B 17/0057 289/1.2 |
| 8,562,629 B2 * | 10/2013 | Bain | .................. | A61B 17/0469 606/144 |
| 8,821,545 B2 * | 9/2014 | Sengun | ............. | A61B 17/0401 289/1.5 |
| 8,956,372 B2 * | 2/2015 | Fenton | ............. | A61B 17/06166 606/144 |
| 9,078,633 B2 * | 7/2015 | Belson | ............. | A61B 17/0057 |
| 2004/0116943 A1 | 7/2004 | Brandt et al. | | |
| 2004/0127915 A1 * | 7/2004 | Fleenor | ............. | A61B 17/0469 606/144 |
| 2004/0147941 A1 * | 7/2004 | Takemoto | .......... | A61B 17/0469 606/144 |
| 2004/0186514 A1 * | 9/2004 | Swain | ............... | A61B 17/0401 606/224 |
| 2005/0149067 A1 * | 7/2005 | Takemoto | .......... | A61B 17/0469 606/144 |
| 2005/0228406 A1 * | 10/2005 | Bose | .................. | A61B 17/0469 606/144 |
| 2006/0264975 A1 | 11/2006 | Pipenhagen et al. | | |
| 2008/0228224 A1 | 9/2008 | Sauer | | |
| 2008/0269783 A1 | 10/2008 | Griffith | | |
| 2009/0018554 A1 * | 1/2009 | Thorne | ............. | A61B 17/0485 606/145 |
| 2009/0306711 A1 * | 12/2009 | Stone | ................. | A61B 17/0401 606/232 |
| 2011/0077667 A1 * | 3/2011 | Singhatat | ........... | A61B 17/0401 606/139 |
| 2011/0144666 A1 * | 6/2011 | Egle | ................... | A61B 17/0469 606/144 |
| 2012/0245629 A1 * | 9/2012 | Gross | ............... | A61B 17/06166 606/228 |
| 2012/0277770 A1 * | 11/2012 | Fenton | ............. | A61B 17/06166 606/151 |
| 2013/0296895 A1 * | 11/2013 | Sengun | ............. | A61B 17/0401 606/148 |
| 2013/0296896 A1 * | 11/2013 | Sengun | ............. | A61B 17/0401 606/148 |
| 2013/0296931 A1 * | 11/2013 | Sengun | ............. | A61B 17/0401 606/228 |
| 2013/0296934 A1 * | 11/2013 | Sengun | ............. | A61B 17/0401 606/232 |

OTHER PUBLICATIONS

European Search Report for 10781131.7-1654 / 2434962 PCT/US2010036190, dated Nov. 27, 2014.

* cited by examiner

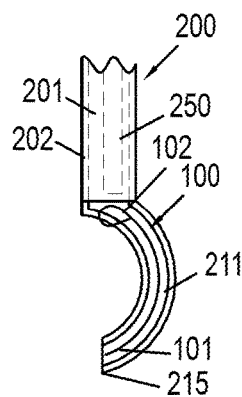 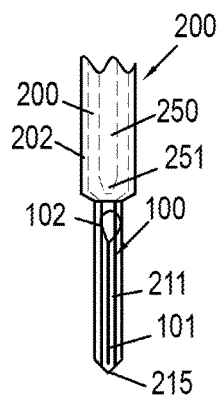 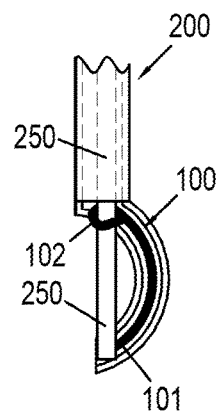 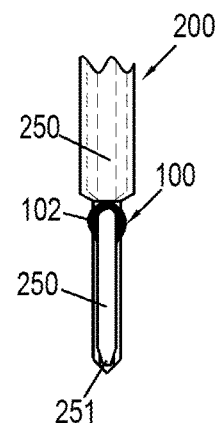
Fig. 3a  Fig. 3b  Fig. 3c  Fig. 3d
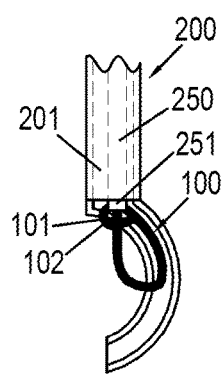 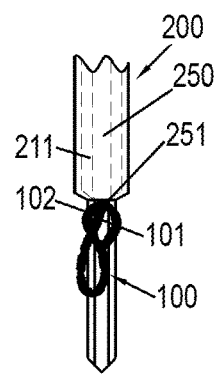 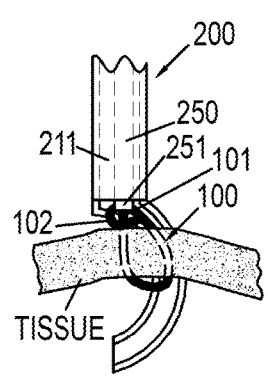 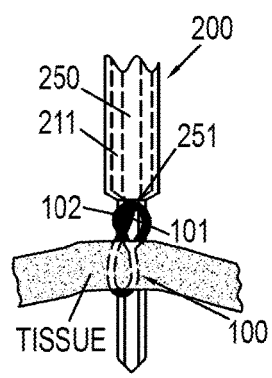
Fig. 3e  Fig. 3f  Fig. 3g  Fig. 3h

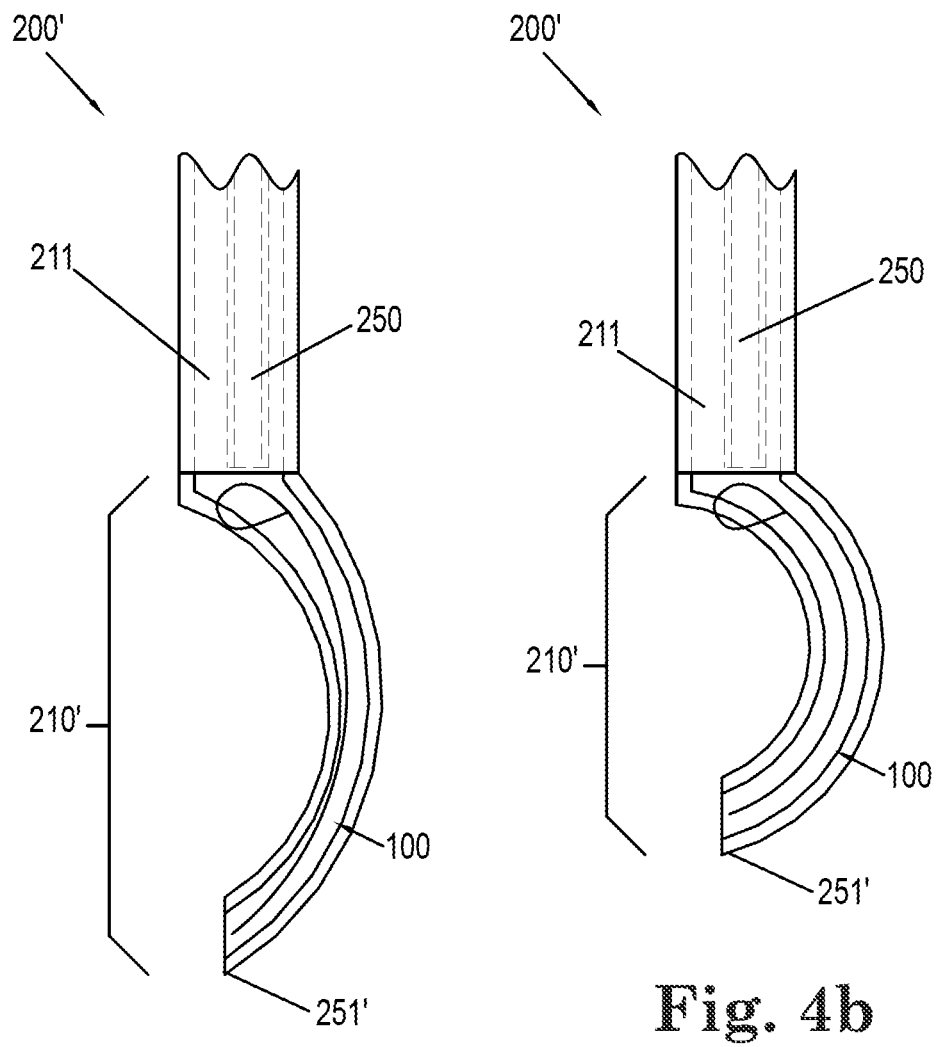

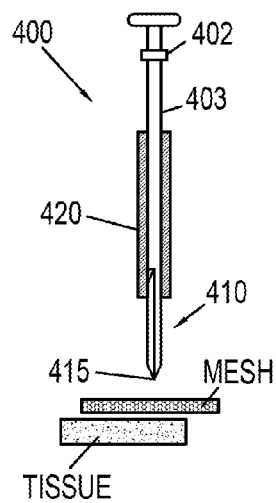
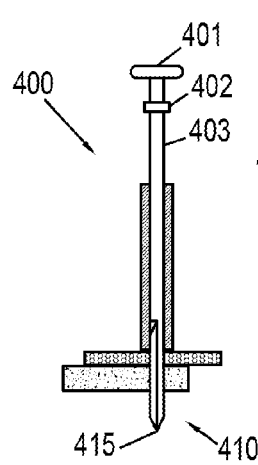
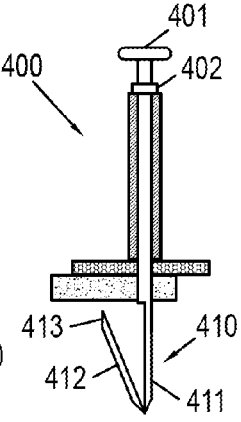
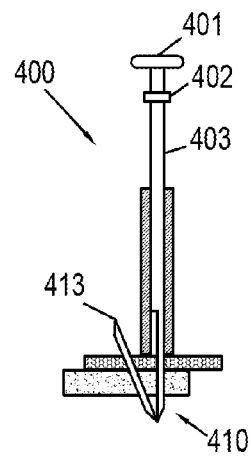
Fig. 7a  Fig. 7b  Fig. 7c  Fig. 7d
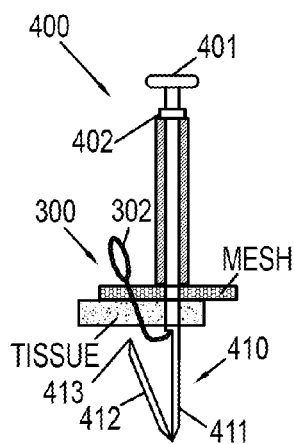
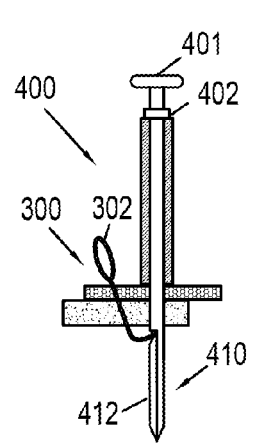
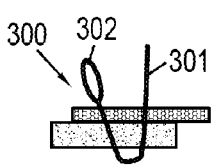
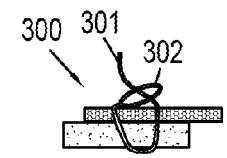
Fig. 7e  Fig. 7f  Fig. 7g  Fig. 7h

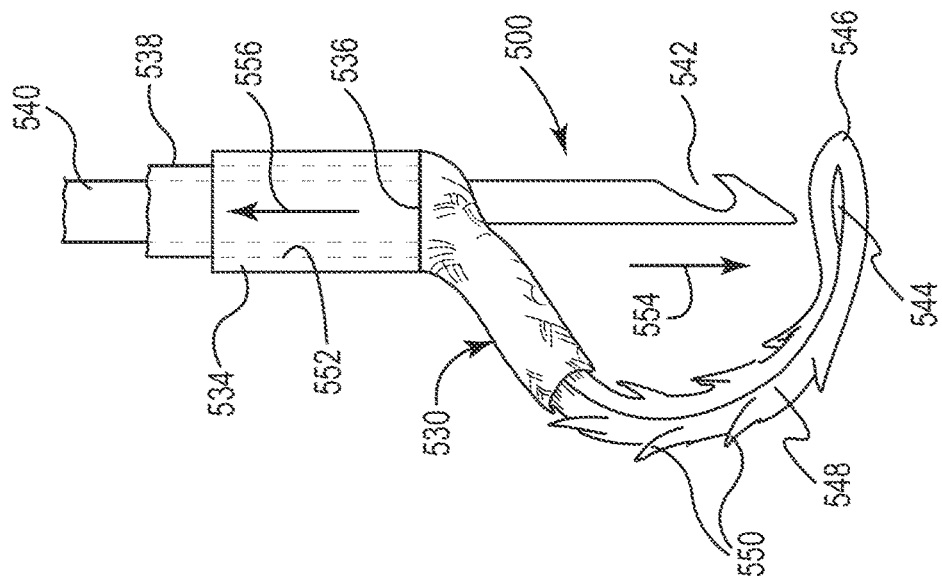
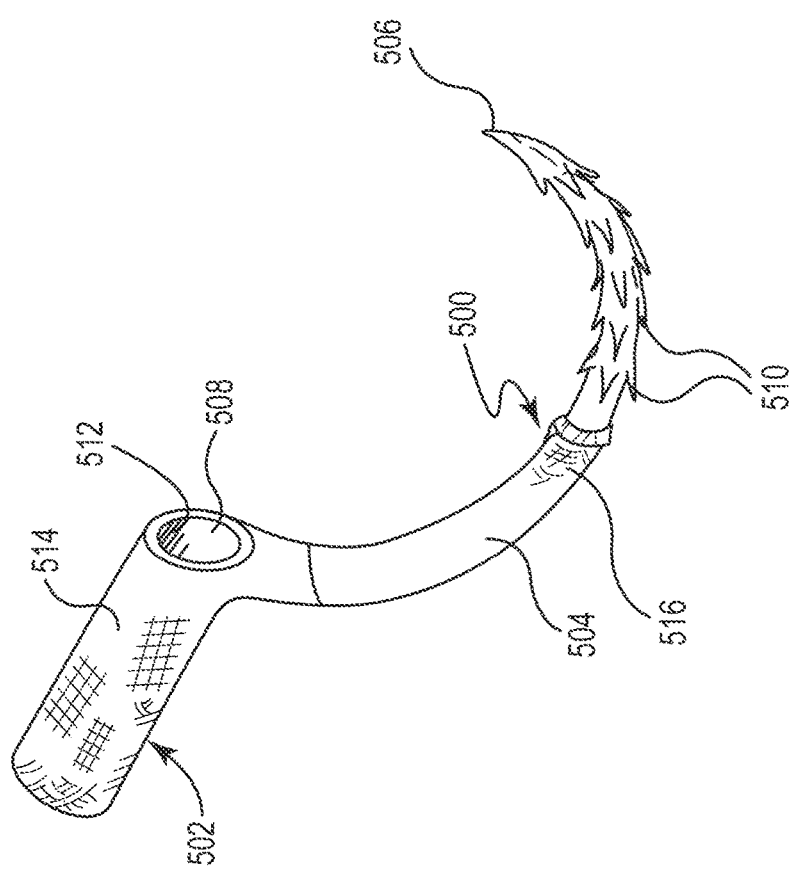

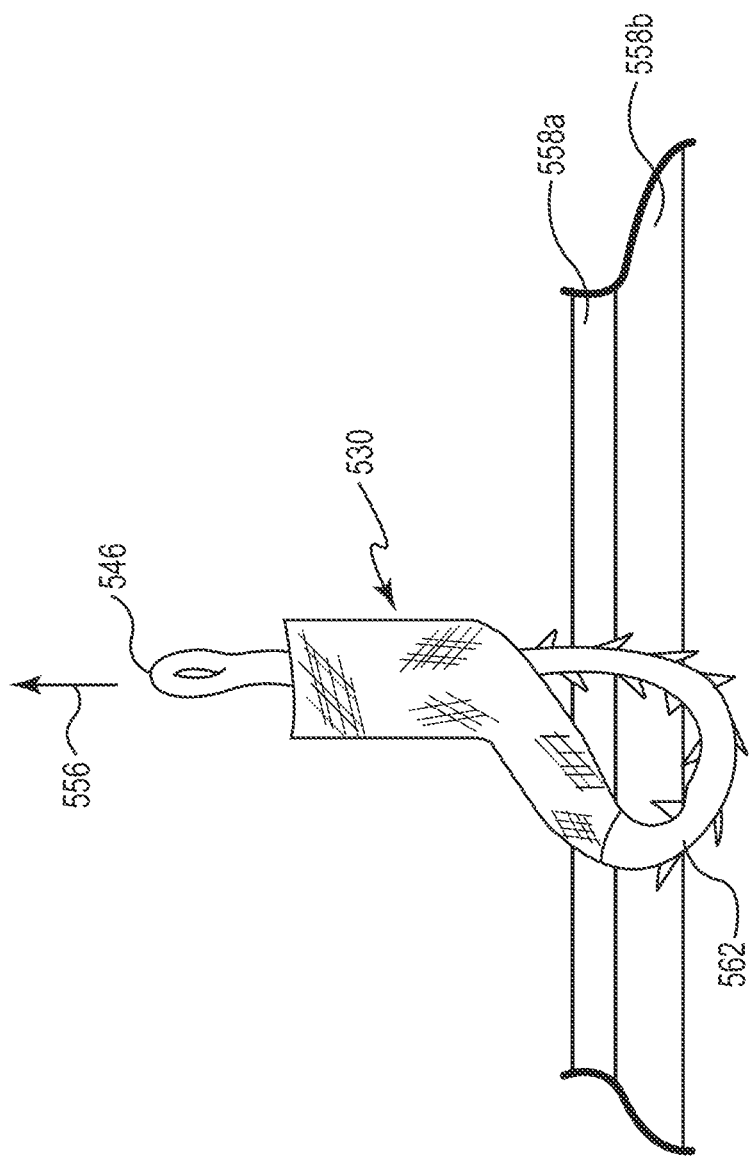

FILAMENTOUS TISSUE IMPLANT

The present application is a continuation of U.S. patent application Ser. No. 13/383,956, entitled Filamentous Tissue Implant, filed May 3, 2012 (Allowed), which claims the benefit of PCT/US2010/036190, entitled Filamentous Tissue Implant, filed May 26, 2010, which claims the benefit of U.S. Provisional Patent Application Ser. No. 61/180,935, entitled Filamentous Tissue Implant, filed May 26, 2009.

FIELD OF THE INVENTION

The present disclosure relates generally to tissue fixation devices, systems and methods. In particular, the present disclosure provides a tissue fastening device which provides simplified fixation of tissue to structures such as implantable mesh and other tissue.

BACKGROUND OF THE INVENTION

Numerous devices have been used to fasten tissue to another structure, including other tissue. Filament is provided in various types, used in combination with a needle to sew tissue. Mechanical clips are used to mechanically fixate tissue, similar to stapling. Many tissue fixation devices and methods are dependent on technique and can result in adequate attachment or undesirable long term effects such as scarring. There is therefore a need for improved tissue fixation devices, systems and methods.

BRIEF SUMMARY OF THE INVENTION

The present disclosure is directed to several unique tissue fasteners, tissue fixation systems and tissue fixation methods that provide simplified, repeatable and reliable fixation of tissue to one or more structures and/or to other tissue.

One embodiment of the tissue fixation system includes a delivery tube and an elongated fastener with a loop at a proximal end and a distal end. A proximal end of an elongated curved needle is attached to the delivery tube. A distal end of the needle is configured to penetrate or encircle tissue. The needle includes an open channel sized to receive the elongated fastener with the loop located near the proximal end of the elongated curved needle and the distal end of the elongated fastener located near the distal end of the elongated curved needle. A capture needle is slidably positioned in the delivery tube to slide through the loop in the proximal end of the elongated fastener. The capture needle is configured to grasp the distal end of the elongated fastener and pull the distal end of the elongated fastener through the loop to cinch the elongated fastener.

The capture needle preferably mechanically engages with the distal end of the elongated fastener. The distal end of the elongated fastener optionally includes a loop.

The proximal end of the elongated fastener can be multi-filament structure and the distal portion of the elongated fastener includes one or more interlock structures configured to self-lock with the proximal end.

In another embodiment, the proximal end is a hollow multi-filament sleeve sized to receive, and self-lock with interlock structures formed at the distal end of the fastener. The interlock structures are configured to penetrate the proximal end. Alternatively, the interlock structures can be located along an interior surface of the sleeve portion. In one embodiment, the distal portion of the elongated fastener is a monofilament and the multi-filament sleeve extends along a portion of the monofilament.

Interlock structure can be prongs, barbs, protrusions, hooks, extensions, teeth, textured surfaces, and the like. The interlock structures can be discrete features added to the self-locking fastener; molded or extruded as part of the self-locking fastener; formed by post-processing the self-locking fastener; and/or a variety of other approaches. In one embodiment, the first portion of the fastener is a loop structure and the second portion is a hook structure, such as in a hook-and-loop fastener.

The elongated fastener optionally includes rigid portions. The distal end of the elongated fastener optionally deforms either plastically or elastically. The elongated fastener is optionally bioabsorbable material. The elongated fastener can be constructed of a material selected from the group consisting of: polylactide, polyglycolide, polysaccharides, proteins, polyesters, polyhydroxyal kanoates, polyalkelene esters, polyamides, polycaprolactone, polyvinyl esters, polyamide esters, polyvinyl alcohols, polyanhydrides polyolefins, PEEK, PTFE, and their copolymers, modified derivatives of caprolactone polymers, polytrimethylene carbonate, polyacrylates, polyethylene glycol, hydrogels, photo-curable hydrogels, terminal diols, and combinations thereof. The elongated fastener optionally includes metal filaments, such as for example Nitinol, configured to provide a resilient bias, either along, or in combination with polymeric filaments.

In one embodiment, the curved needle includes a rolled sheet. The open channel is created by unrolling the penetrating portion. In another embodiment, the capture needle includes jaws configured to transition from an open to a closed position. An energy source is optionally provided to bond distal end of the elongated fastener to the loop. The energy can be one or more of heat and/or ultrasonic energy.

The present disclosure is also directed to a method of engaging the tissue fixation system with two or more layers of material. The elongated fastener is loaded in the open channel of the elongated curved needle with the loop located near the proximal end of the elongated curved needle and the distal end of the elongated fastener located near the distal end of the elongated curved needle. The distal end of the curved needled is inserted through two or more layers of material. The capture needle is advanced through the delivery tube and through the loop in the proximal end of the elongated fastener. The capture needle is engaged with the distal end of the elongated fastener. The capture needle is retracted to pull the distal end of the elongated fastener through the loop to cinch the elongated fastener. The delivery tube and the needle are separated from the elongated fastener.

In another embodiment, the delivery device is a multi-fire instrument that retains and delivers a plurality of fasteners. The fasteners can be delivered sequentially or in parallel. The present delivered device can be mounted to a variety of other instruments, such as for example, an endoscope.

BRIEF DESCRIPTION OF THE SEVERAL VIEWS OF THE DRAWING

The accompanying drawings, which are incorporated in and constitute a part of this specification, illustrate various embodiments of the present disclosure, and, together with the description, serve to explain the principles of the disclosure. In the drawings:

FIGS. 3a through 3h illustrate a method of tissue fixation utilizing the system of FIGS. 2a and 2b in accordance with an embodiment of the present disclosure.

FIG. 4a illustrates a side view of a fixation system deployed in an elongated, rigid state in accordance with an embodiment of the present disclosure.

FIG. 4b illustrates a side view of the fixation system of FIG. 4a deployed in a contracted, flexible state.

FIGS. 7a through 7h illustrate a method of tissue fixation utilizing the system of FIGS. 6a and 6b in accordance with an embodiment of the present disclosure.

FIG. 10 is a perspective view of a self-locking fastener in accordance with an embodiment of the present disclosure.

FIG. 11 is a perspective view of an alternate self-locking fastener in accordance with an embodiment of the present disclosure.

FIG. 12d illustrates the self-locking fastener of FIG. 11 secured to two adjacent layer of material in accordance with an embodiment of the present invention.

DETAILED DESCRIPTION OF THE INVENTION

Reference will now be made in detail to the present embodiments of the disclosure, examples of which are illustrated in the accompanying drawings. Wherever possible, the same reference numbers will be used throughout the drawings to refer to the same or like parts.

The present disclosure provides devices, systems and method for coapting or otherwise attaching tissue of a patient to a structure. Tissue fixation is used in many medical procedures, such as tissue repair procedures, or procedures which cause the need for tissue repair. Numerous types of tissue may require fixation, such as ligaments and skin.

To facilitate an understanding of the disclosure, a number of terms are defined below.

As used herein, the terms "subject" and "patient" refer to any animal, such as a mammal like livestock, pets, and preferably a human. Specific examples of "subjects" and "patients" include, but are not limited, to individuals requiring medical assistance, and in particular, requiring tissue fixation.

The present disclosure provides structures that embody aspects of the tissue fixation system. The present disclosure also provides fasteners implanting in a patient for coapting tissue to a separate structure, such as an implantable mesh or other patient tissue. The illustrated and preferred embodiments discuss these structures and techniques in the context of tissue fixation. These structures, systems, and techniques are well suited for use in the field of surgery and other medical procedures. However, it should be appreciated that the disclosure is applicable for use in other applications that affix a first structure to a second structure. The fixation devices, systems and method of the present disclosure have advantages over previous prior art devices. FIGS. 1-9 show various preferred embodiments of the fixation devices and systems of the present disclosure. The present disclosure is not limited to these particular configurations.

Figure 1:
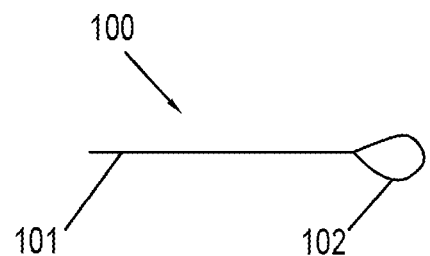
FIG. 1 illustrates a side view of a fastener in accordance with an embodiment of the present disclosure.

Referring now to FIG. 1, a preferred embodiment of a tissue fastener of the present disclosure is illustrated. Fastener 100 includes a first end 101, and a second end, loop 102. Fastener 100 is configured to be used with one or more delivery assemblies used by a clinician such as a surgeon, to implant or otherwise deploy fastener 100 between tissue of a patient, and a second structure. Fastener 100 is a filamentous structure constructed of one or more polymeric materials such as for example, a filament material. Fastener 100 may be made of materials which will remain intact, permanently implanted over long periods of time, such as times greater than about 6 months, or more than about 24 months.

Alternatively, fastener 100 may be made of materials which bioabsorb, such as at a bioabsorption rate of more than about two years to less than about one month, or less than seven days. Numerous materials have been developed to be absorbed by the body, such as a magnesium reinforced polymer. Numerous polymers can be used such as polymers selected from the group consisting of: polylactide, polyglycolide, polysaccharides, proteins, polyesters, polyhydroxyalkanoates, polyalkelene esters, polyamides, polycaprolactone, polyvinyl esters, polyamide esters, polyvinyl alcohols, polyanhydrides, polyolefins, PEEK, PTFE, and their copolymers, modified derivatives of caprolactone polymers, polytrimethylene carbonate, polyacrylates, polyethylene glycol, hydrogels, photo-curable hydrogels, terminal diols, and combinations of these. Bioabsorbable fibers that reinforce a bioabsorbable polymer matrix can be used. Filament materials can be made in permanent or absorbable matrices.

In an alternative embodiment, fastener 100 has a permanent portion, such as a portion including loop 102 and neighboring material, and an absorbable portion such as a portion including end 101. In this configuration, end 101 and neighboring portions are used to assist in deployment and cinching of fastener 100. However once deployed, end 101 and neighboring portions are unnecessary for fixation and are bioabsorbed.

Figure 2A:
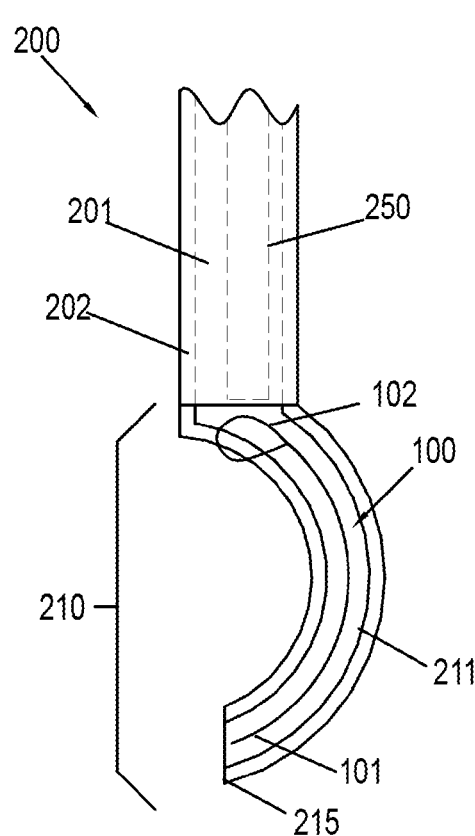
FIGS. 2a and 2b illustrate front and side views of a fixation system in accordance with an embodiment of the present disclosure.
Figure 2B:
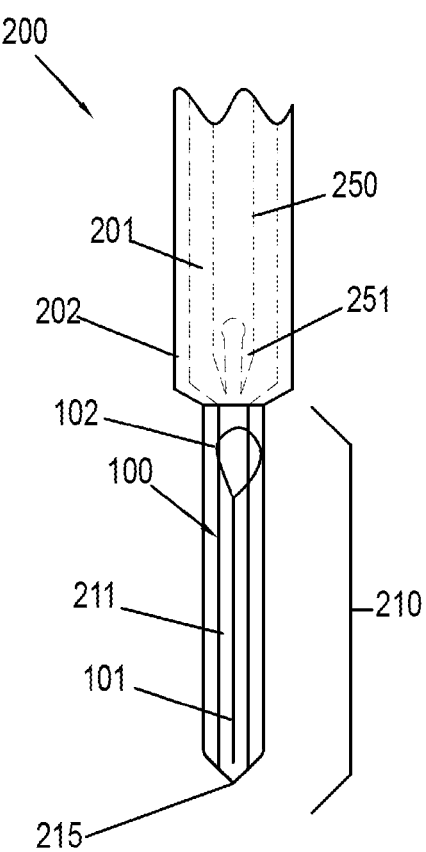

Referring now to FIGS. 2a and 2b, side and top views of a preferred embodiment of a fixation system in accordance with an embodiment of the present disclosure are illustrated. A system includes fastener 100, preferably similar in construction to fastener 100 of FIG. 1, which is configured to be deployed using delivery assembly 200. A clinician, such as a surgeon, uses delivery tool 200 to coapt tissue of a patient, to a structure, such as a mesh or additional tissue of the patient. The mesh can be used to create a support structure such as in a hernia repair procedure or other procedure in which an additional support is beneficial. Numerous biocompatible mesh materials can be used such as Dacron mesh. The mesh can be placed within the body or on the surface of the skin such as in a procedure treating one or more patient burns.

Delivery tool 200 includes an elongate tube, housing 202 with internal lumen 201. Housing 202 is preferably rigid, but may be flexible or include flexible portions such as hinged portions. Housing 202 may be configured to transition from rigid to flexible or vice versa, such as via a mechanism, not shown but preferably selected from the group consisting of: hydraulic or pneumatic chambers, embedded shaped memory material, insertable pre-shaped mandrels and combinations of these.

Housing 202 may include one or more markers, not shown but preferably markers selected form the group consisting of visible markers, ultrasonically reflective markers, radiopaque markers, electromagnetic markers, and combinations of these. These markers may be used to determine an insertion depth (e.g. into tissue) and/or otherwise orient delivery tool 200 for tissue fixation or tool removal.

Housing 202 may have a circular cross-section, or alternative geometries may be employed. In alternative embodiments, cross-sectional geometry may be oval, square, rectangular or trapezoidal, such as to create a preferred bending moment or for preferred insertion of one or more devices into housing 202. Housing 202 may include one or more hinged portions, such as to allow controlled bending of housing 202 prior to, during or after tissue fixation.

Housing 202 is fixedly attached to penetrating portion 210, configured to penetrate through the patient's tissue and any other material to be coapted to the patient's tissue. Penetrating portion 210 is shown as a curved needle construction, preferably rigid but alternatively constructed to controllably transition from flexible to rigid or vice versa as has been described above and is described below in reference to FIGS. 4a and 4b. Penetrating portion 210 includes a channel 211 which is configured to receive fastener 100, with loop 102 at the proximal end of penetrating portion 210 (proximal to housing 202) and end 101 at the distal end of penetration portion 210. The distal end of penetrating portion 210 includes sharpened tip 215, such as a pointed or beveled needle tip, configured to penetrated tissue and the structure that the tissue is to be fixated to. In a preferred embodiment, tip 215 has a sharp leading edge with a blunted trailing edge to avoid coring of tissue during insertion.

Penetrating portion 210 includes an opening, channel 211 which is sized to allow fastener 100 to pass out of penetrating portion 210 during the fixation procedure. Channel 211 is preferably sized to approximate the relative diameter of fastener 100. In an alternative embodiment, penetration portion 210 comprises a rolled sheet of material, such as rolled Nitinol or stainless steel sheet, and an opening is formed by unfurling (unrolling) the sheet.

Delivery tool 200 further includes a grasping assembly, grasper 250 which is slidingly received by housing 202 in lumen 201. Grasper 250 includes deployable jaws 251 at its distal end. Grasper 250 is advanced through loop 102 of fastener 100 to a location proximate end 101 of fastener 100.

Jaws 251 are operated to grasp end 101 and retract end 101 in order to cinch fastener 100 to tissue, as is described in detail in reference to FIGS. 3a through 3h. Grasper 250 is preferably connected to a control such as a slide on a handle, control and handle not shown but of similar construction to medical device handles and linkage controls, well known to those of skill in the art.

In an alternative embodiment, delivery tool 200 and the various fastener delivery tools of the present disclosure, include a power supply such as a battery and electronics used to operably control one or more mechanisms of delivery tool 200, and/or to deliver energy such as heating or welding energy used to cinch fastener 100. Activation of delivery tool 200 may be manual, such as via linkages and other controls integral to tool 200, or automatic or semi-automatic, such as via a control that activates a circuit controlling an electromechanical assembly such as an assembly including a motor, solenoid, or a piezo crystal.

In another alternative embodiment, delivery tool 200 includes attachment means configured to controllably maintain position of fastener 100 in penetrating portion 200, and actively release fastener 100 during or after fixation, attachment means not shown but preferably activated by a control on a handle of delivery tool 200.

In yet another alternative embodiment, the tissue fixation system is provided in a kit form, including two or more fasteners. The two or more fasteners may be identical, or may have different features such as features selected from the group consisting of: geometry such as pre-deployed geometry and deployed (cinch) geometry, length, width, stiffness, implantation life, melt temperature, and combinations of these.

Referring now to FIGS. 3a through 3h, paired side and top views of a preferred method of tissue fixation using the system of FIGS. 2a and 2b is illustrated. FIGS. 3a and 3b illustrate side and top views, respectively, of a first step in which delivery tool 200 and fastener 100 are in a state ready for penetration into tissue (tissue and structure to be fixated not shown). FIGS. 3c and 3d illustrate side and top views, respectively, of a subsequent step in which delivery tool 200 and fastener 100 have been inserted into tissue and a structure, grasper 250 has been advanced through loop 102 of fastener 100, and jaws 251 have grasped end 101 of fastener 100 (tissue and structure not shown). FIGS. 3e and 3f illustrate side and top views, respectively, of a subsequent step in which grasper 250 has been retracted such that end 101 is pulled through loop 102 (tissue and structure to be fixated not shown). FIGS. 3g and 3h illustrate top and side views, respectively, of the step of FIGS. 3e and 3f, with tissue shown (fixated structure not shown). In a subsequent step, not shown, jaws 251 of grasper 250 would open to release end 101 of fastener 100, and penetrating portion 210 of delivery tool 200 would be retracted form the tissue, leaving fastener 100 in place in the tissue (fixated structure not shown).

Fastener 100 can be left as described immediately above, with a frictional engagement. Alternatively or additionally, fastener 100 can be further secured, such as via adhesive (not shown but preferably an adhesive delivery mechanism integral to delivery tool 200). Alternatively or additionally, fastener 100 can be further secured, such as via heating or welding by delivery tool 200 (not shown but preferably an energy delivery mechanism integral to delivery tool 200), or any other physical or chemical method of bonding. As used herein, "bond" or "bonding" refers to, for example, physical, mechanical, and/or chemical techniques, such as for example, adhesive bonding, solvent bonding, ultrasonic welding, thermal bonding, suitable for securing ends of a fastener.

Referring now to FIGS. 4a and 4b, a preferred embodiment of a fixation system of the present disclosure is illustrated. Delivery tool 200' is similar in construction and function to delivery tool 200 of FIGS. 2a and 2b, but is additionally configured to have penetrating portion 210' transition from a rigid state to a flexible or semi-rigid state, and/or vice versa. Alternatively or additionally, delivery tool 200' is configured to change geometry, such as to transition from an expanded state to a contracted state, and/or vice versa. Referring specifically to FIG. 4a, penetrating portion 210' is shown in an expanded, rigid state.

Referring specifically to FIG. 5b, penetrating portion 210' is shown in a contracted, semi-rigid state. Rigidity may be manipulated to encircle tissue and establish tissue penetrating pathways. Rigidity may be manipulated prior to or during insertion, or prior to or during retraction. In a preferred embodiment, the rigidity and/or shaping is achieved by changing states of a shaped memory material, such as via a temperature change. Alternatively or additionally, the rigidity and/or shaping are achieved through the use of one or more of: hydraulics, pneumatics, or insertion of a pre-shaped or shapeable mandrel. Tip 251' can selectively be made rigid, semi-rigid or flexible to allow for access to restricted spaces. State change can be performed prior to movement, or to be formed into a preferred position. Rigidity and/or shape change is preferably activated by a control on a handle to delivery tool 200' (handle and control not shown). Activation can be accomplished with an electromechanical assembly, such as a battery-controlled module configured to heat a Nitinol wire, causing contraction. Alternatively or additionally, other mechanical components can be employed such as springs, cams and/or levers.

Figure 5:
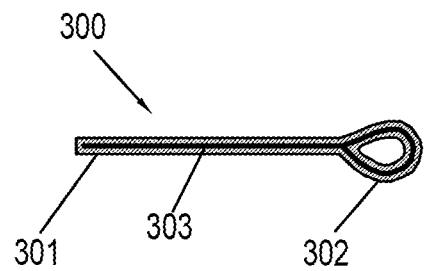
FIG. 5 illustrates a side view of a fastener with an inner member in accordance with an embodiment of the present disclosure.

Referring now to FIG. 5, another preferred embodiment of a tissue fastener of the present disclosure is illustrated. Fastener 300 includes a first end 301, and a second end, loop 302. Fastener 300 is configured to be used with one or more delivery assemblies used by a clinician such as a surgeon, to implant or otherwise deploy fastener 100 between tissue of a patient, and a second structure. Fastener 300 is a filamentous structure constructed of one or more polymeric materials, such as for example, a filament material. Fastener 300 may be made of materials which will remain intact, permanently implanted over long periods of time, such as times greater than about 6 months, or more than about 24 months. Alternatively, fastener 100 may be made of materials which bioabsorb, such as has been described above in reference to FIG. 1.

Fastener 300 further includes insert 303, an elongate structure within the outer surface of fastener 300. In one embodiment, insert 303 is a malleable filament configured to allow fastener 300 to plastically deform and maintain the deformed shape, such as prior to, during, or after fixation of tissue to a structure. In an alternative embodiment, insert 303 is a resiliently biased material, such as a material configured to maintain the relatively linear geometry shown in FIG. 5, or to bias fastener 300 in the cinched state (cinched bias not shown).

Figure 6A:
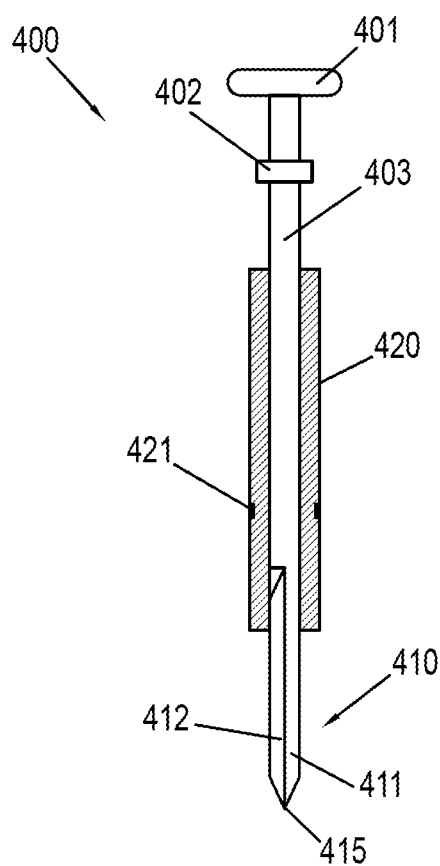
FIG. 6a illustrates a side sectional view of a fixation system shown in the retracted state in accordance with an embodiment of the present disclosure.
Figure 6B:
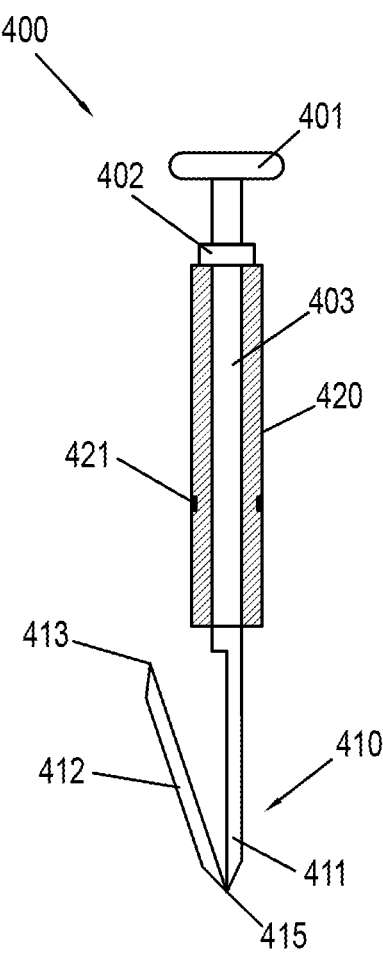
FIG. 6b illustrates a side sectional view of the fixation system of FIG. 6a shown in a deployed configuration.

Referring now to FIGS. 6a and 6b, a preferred embodiment of a tissue delivery tool of the present disclosure is illustrated. Delivery tool 400 includes housing 420 which slidingly receives shaft 403. Housing 420 may be made of rigid, semi rigid or flexible materials. Alternatively, housing 420 may be configured to transition from rigid to flexible, and/or vice versa, as has been described in detail above. Shaft 403 has a proximal end and a distal end. On the proximal end of shaft 503 is knob 401. Shaft 403 further includes step 402 which is configured to limit advancement of shaft 403 into housing 420. In a preferred embodiment, stop 402 is adjustable such as via sliding or rotating stop 402 along shaft 420. Shaft 520 includes insertion line 421, which is used by an operator such as a clinician to properly advance or position delivery tool 400 into tissue or otherwise. Line 421 may be a visible marker, a radiopaque marker, an ultrasonically reflective surface, an electromagnetic marker, or combinations of these.

At the distal end of shaft 420 is expandable needle assembly 410. Needle assembly 410 includes stationary needle 411 and pivoting needle 412. Stationary needle 411 is rotatably attached to pivoting needle 412 at tip 415, pivot not shown but preferably a miniature hinge configured to be closed by rotation of knob 401. Alternatively or additionally, needle assembly 410 may be expanded or contracted through activation of a shape memory alloy such as Nitinol. Tip 415 is a sharpened tip configured to penetrate tissue and the structure to be fixated to the tissue. Tip 415 is preferably configured to avoid coring of tissue.

Referring specifically to FIG. 6a, delivery tool 400 is shown with shaft 403 retracted and needle assembly 410 in a compacted state maintained within housing 420. In FIG. 6b, needle assembly 410 is expanded, either by resilient bias or a controllable hinge, such as a hinge opened by rotation of knob 401. In operation, and as described in reference to FIGS. 7a through 7h, needle assembly 410 of delivery tool 400 surrounds a fastener, such as a fastener described in reference to FIG. 1 or FIG. 5. When needle assembly 410 is in the expanded state of FIG. 6b, the fastener is able to exit both stationary needle 411 and pivoting needle 412, via a slot or other opening in each, slots not shown but described in detail in reference to FIGS. 7a through 7h.

Referring now to FIGS. 7a through 7h, side sectional views of a preferred method of tissue fixation using the system of FIGS. 6a and 6b is illustrated. In FIG. 7a, delivery tool 400 is positioned with tip 415 above a mesh which is above tissue to which the mesh is to be coapted. The mesh may be a Dacron or other biocompatible mesh that is often affixed to tissue. Alternatively, the tissue may be affixed to other tissue, such as when two pieces of tissue are closed together in a surgical procedure. Shaft 403 is positioned such that needle assembly 410 is in its compacted state within housing 420. A fastener 300, such as fastener 300 of FIG. 5, has been previously loaded into needle assembly 410.

FIG. 7b illustrates a subsequent step in which tip 415 has been advanced through the mesh and tissue, but shaft 403 has not moved relative to housing 420. In a preferred embodiment, shaft 403 may be maintained in relative position to 420 during insertion, such as via a set screw, compressible collar, movable mechanical stop, or other frictional or mechanical engagement means, engagement means not shown.

FIG. 7c illustrates a subsequent step in which shaft 403 has been advanced such that needle assembly 410 exits housing 420 and expands into a "V" configuration. Pivoting needle 412 rotates away from stationary needle 411 at tip 415. Fastener 300 remains within needle assembly 410, however fastener 300 expands in the same geometry as needle assembly 410. Fastener 300 may be held in place by holding means, not shown, or may be shaped such as to maintain in place.

FIG. 7d illustrates a subsequent step in which the distal end of pivoting needle 412, tip 413, has advanced through the tissue and then the mesh, in the "V" configuration, as shaft 403 is retracted (housing 420 is kept in place).

FIG. 7e illustrates a subsequent step in which fastener 300 has passed through an opening in pivoting needle 412 (opening not shown but preferably oriented toward stationary needle 411. Fastener 300 may have been mechanically released such as via a pull wire or other techniques. Needle assembly 410 is advanced such that tip 413 moves distally and out of the tissue-mesh interface, leaving fastener 300 in place which loop 302 positioned above the mesh.

FIG. 7f illustrates a subsequent step in which pivoting needle 412 has rotated such that needle assembly 410 is in its compact, linear state. Rotation of pivoting needle 412 is accomplished by a controllable bias, a controllable hinge, or other manual or automatic pivoting means. In one embodiment, a collar is attached to a pull wire, the collar surrounding and compacting needle assembly 410, collar not shown. Advancement of the collar allows needle assembly 410 to expand with pivoting needle 412 pivoting away from stationary needle 411. Refraction of the collar capture pivoting needle 412, pivoting it toward stationary needle 411 until the collar surrounds pivoting needle 412 and stationary needle, maintaining needle assembly 410 in its compact, linear state.

FIG. 7g illustrates a subsequent step in which delivery tool 400 has been retracted and removed from the tissue and mesh, leaving fastener 300 in place with loop 302 above the mesh, the middle portion of fastener 300 extending from the top of the mesh to the bottom of the tissue, then from the bottom of the tissue to the top of the mesh, with end 101 above the mesh.

FIG. 7h illustrates a subsequent step in which end 301 has been passed through loop 302 and fastener 300 is ready to be cinched tight, fixating the mesh to the tissue. Alternatively or additionally, loop 302 and end 301 can be fixedly attached with glue, heat and/or welding, as has been described above.

Figure 8:
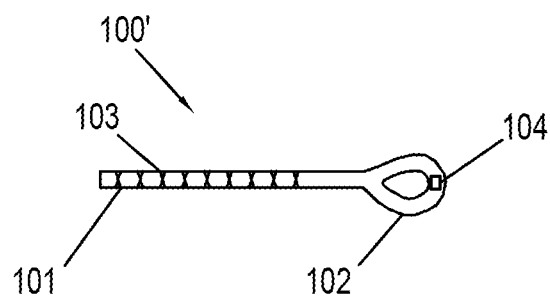
FIG. 8 illustrates a side view of a fastener including multiple detachment points in accordance with an embodiment of the present disclosure.

Referring now to FIG. 8, a side view of a preferred embodiment of a fastener of the present disclosure is illustrated. Fastener 100' includes end 101 and opposite end, loop 102. Along the mid-portion of fastener 100' are notches 103, configured to allow an operator to detach a selectable portion of fastener 100' after end 101 has passes through loop 102 and fastener 100' has been cinched around tissue and/or a structure. Fastener 100' further includes marker 104, such as a visible, radiopaque, ultrasonic, or electromagnetic marker configured to assist in placement of fastener 100' and/or confirm subsequent fixation of fastener 100'.

Figure 9:
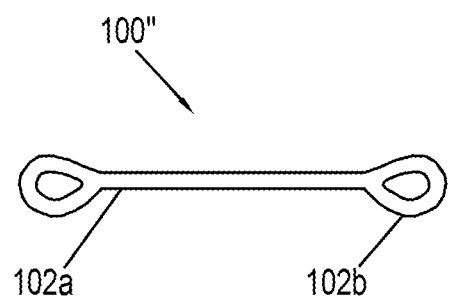
FIG. 9 illustrates a fastener including a loop on each end in accordance with an embodiment of the present disclosure.

Referring now to FIG. 9, a side view of another preferred embodiment of a fastener of the present disclosure is illustrated. Fastener 100" includes loop 102a on one end and loop 102b on the other end. Fastener 100" can be used in the various devices of the present disclosure, avoiding the need for orientation of fastener 100". Loop 102a can be configured to pass through loop 102b, as the non-looped ends described above. In another embodiment, multiple loops can be used to perform a function, such as in attachment to other fasteners to provide a loop structure for cinching. Loop 102a and loop 102b may be of similar geometry or construction or different.

FIG. 10 illustrates self-locking fastener 500 in accordance with an embodiment of the present invention. The self-locking fastener 500 includes proximate portion 502 connected to filament portion 504. Distal end 506 of the filament portion 504 is configured to form a self-locking mechanically interlock with the proximate portion 502. As used herein, "self-locking" refers to a mechanical interlock between different portions of a fastener in at least one direction of travel. The self-locking feature is preferably only in one direction so the surgeon can incrementally tighten or cinch as needed.

A variety of self-locking structures can be used. In one embodiment, the self-locking structures include a multi-filament first portion and a second portion having interlock structures that mechanically engaged with the first portion. As used herein, "multi-filament" refers to a variety of structures, such as for example, woven, non-woven, interlaced, perforated, penetrable, braided, and a variety of other structures. The multi-filament portion of the fastener can be a natural material, such as for example, cotton or silk, or a polymeric material, such as polylactide, polyglycolide, polysaccharides, proteins, polyesters, polyhydroxyal kanoates, polyalkelene esters, polyamides, polycaprolactone, polyvinyl esters, polyamide esters, polyvinyl alcohols, polyanhydrides, polyolefins, PEEK, PTFE, Dacron and their copolymers, modified derivatives of caprolactone polymers, polytrimethylene carbonate, polyacrylates, polyethylene glycol, hydrogels, photo-curable hydrogels, terminal diols, and combinations thereof. In some cases filament materials are coated, encapsulated, or blended with antimicrobial substances to reduce chances of wound infections and/or antibiotics and growth proteins for enhance healing of ruptured tissues.

In another embodiment, the self-locking structures include molded, rolled sheets or extruded first and/or second portions that mechanically interlock, with or without the use of a multi-filament portion. A wide variety of interlocking structures are possible, including but not limited to molded structures and structures that are manufactured in multiple steps.

"Interlock structure" refers to prongs, barbs, protrusions, hooks, extensions, teeth, textured surfaces, and the like. The interlock structures can be discrete features added to the self-locking fastener; molded or extruded as part of the self-locking fastener; formed by post-processing the self-locking fastener; and/or a variety of other approaches. In one embodiment, the first portion of the fastener is a loop structure and the second portion is a hook structure, such as in a hook-and-loop fastener.

In the illustrated embodiment, sleeve portion 502 is a hollow, multi-filament material 514 and the filament portion 504 is a monofilament configured to be inserted into opening 508. In an alternate embodiment, the sleeve portion 502 may be a textile structure, extruded tubing, or a molded or roll-formed part.

At least a portion of the filament portion 504 includes a plurality of interlock structures 510 configured to interlock through internal surface 512 of sleeve portion 502. The interlock structures 510 preferably penetrate the multi-filament sleeve portion 502 to form a secure self-locking mechanical interlock. See e.g., FIG. 13. The angle of the interlock structures 510 permit the distal end 506 to advance as far into the opening 508 as needed to tighten the filament portion 504.

The interlock structures 510 are preferably made during a post processing step, such as for example, by creating small cuts in the filament portion 504, as will be discussed in more detail below. Alternatively, the interlock structures 510 can be molded as part of the filament portion 504, overmolded onto the filament portion 501, discrete structures attached or bonded to the filament portion 504, or a variety of other techniques.

In the illustrated embodiment, portion 516 of the multi-filament material 514 extends along a portion of the length of the filament portion 504 to form a permanent connection with the sleeve portion 502. In one embodiment, the portion 516 of the multi-filament material 514 is bonded to the monofilament 504. In another embodiment, portion 516 mechanically engages with interlock structures on the filament portion 504. In yet another embodiment, separate mechanical interlocks, such as for example, pins, staples, bands, can be used to form a permanent connection between the sleeve portion 502 and the filament portion 504.

Figure 12C:
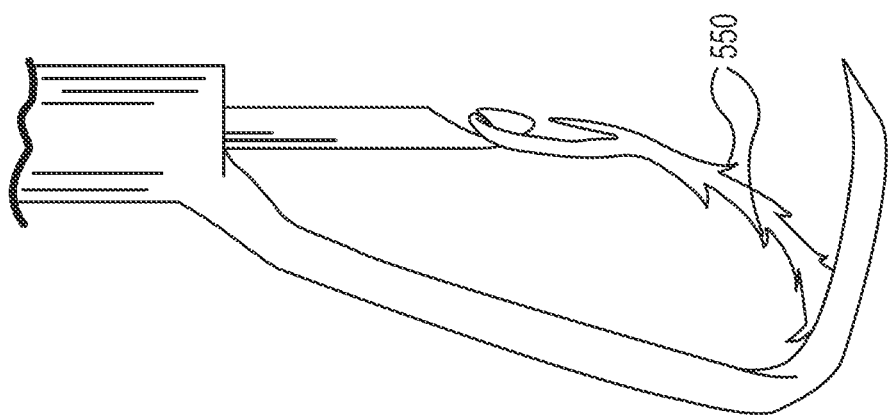
FIGS. 12a-12c illustrates a delivery assembly for a self-locking fastener in accordance with an embodiment of the present disclosure.
Figure 12B:
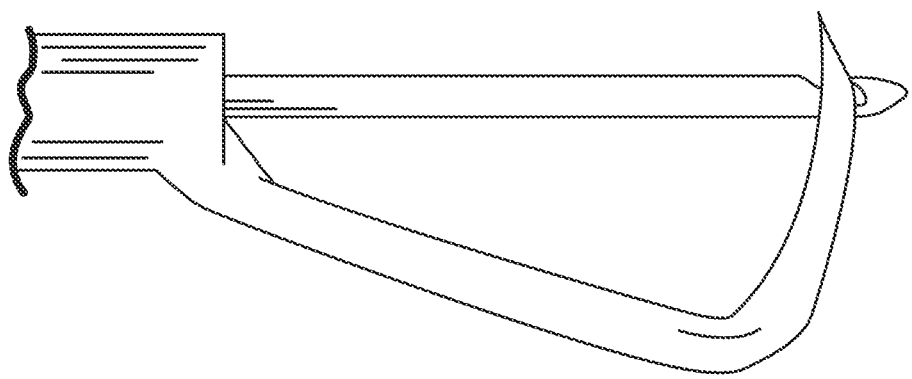
Figure 12A:
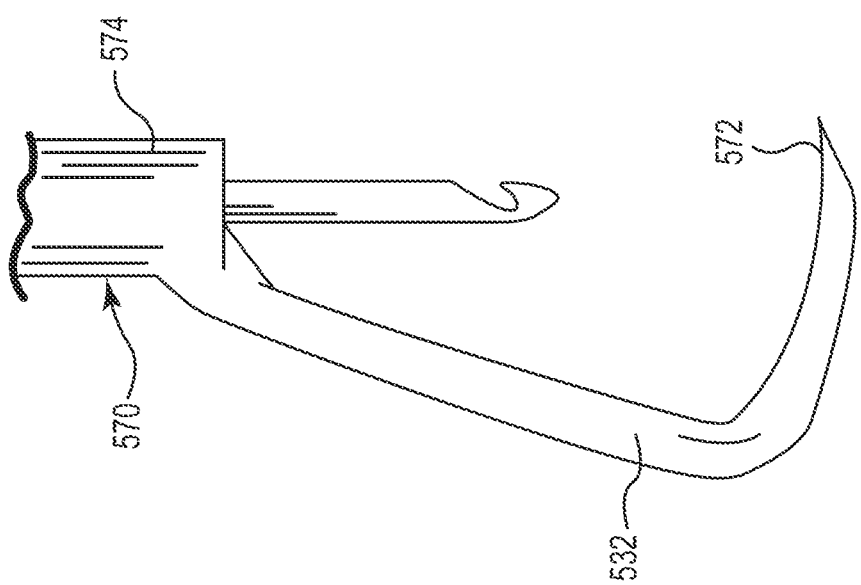

FIG. 11 illustrates an alternate self-locking fastener 530 in accordance with an embodiment of the present disclosure. The penetrating portion 532 illustrated in FIGS. 12a-12c is removed for the sake of clarity. Hollow sleeve portion 534 is fitted on distal end 536 of delivery tube 538. Capture needle 540 extends through delivery tube 538 with hook 542 positioned to engage with loop 544 at distal end 546 of filament portion 548. Interlock structures 550 located on filament portion 548 are configured to self-lock with internal surface 552 of the hollow sleeve portion 534. Once the filament portion 548 is engaged with the hollow sleeve portion 534, the interlock structures 550 resist disengagement in direction 554. The filament portion 548, however, can be advanced further into the hollow sleeve portion 534 in direction 556 to tighten or cinch the self-locking fastener 530.

The loop 544 can be formed using a variety of techniques, such as for example, bending a single strand of filament material 548 back on itself, molding the loop 544 in the distal end 546, attaching a separate loop structure to the distal end 546, and the like. In one embodiment, distal end 546 is a discrete molded component designed to be secured in the penetrating portion 532 and to couple with the capture needle 540. In another embodiment, the distal end 546 is a multi-filament structure that the capture needle 540 can penetrate and capture.

FIG. 12a-12c illustrate operation of the self-locking fastener 530 of FIG. 11 located in delivery assembly 570. The delivery assembly 570 includes penetrating portion 532 with sharp tip 572 to penetrate tissue, bone, reinforcing fabrics, and the like. Filament portion 548 is located in an open channel formed in the penetrating portion 532. Sleeve portion 534 is located within housing 574.

As best illustrated in FIG. 12b, the capture needle 540 extends out of the housing 574 until hook 542 passes through loop 544 and captures the filament portion 548. The capture needle 540 is then retracted into the housing 574 so that interlock structures 550 self-locks with interior surface 552 of the sleeve portion 534. The entire self-locking fastener 530 is then released from the delivery assembly 570. Even with the delivery assembly 570 removed, the surgeon has the option to further tension the distal end 546 of the filament portion 548 further into the sleeve portion 534 to tighten or cinch the fastener 530.

FIG. 12d illustrates self-locking fastener 530 securing layer 558a to layer 558b (collectively "558"). The layers 558 can be tissue, bone, a prosthetic device, such as for example, a reinforcing mesh, and the like. The surgeon can advance distal end 546 in direction 556 to tighten or cinch loop 562 formed by the filament portion 548.

Figure 13A:
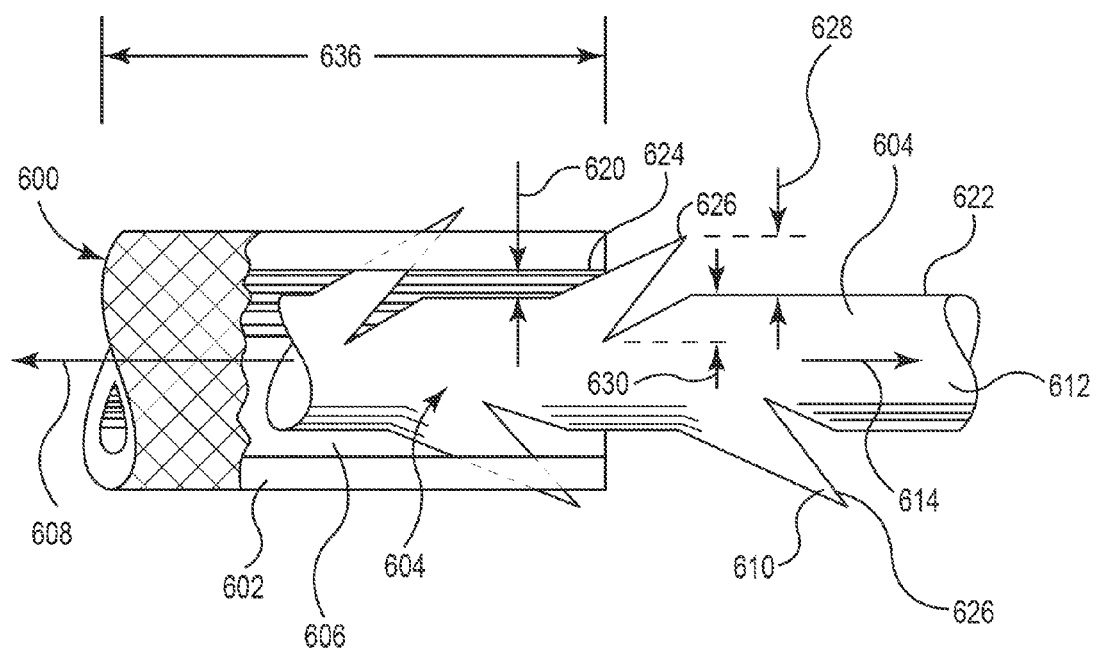
FIG. 13a is a cross-sectional view of a self-locking fastener in a locked configuration in accordance with an embodiment of the present disclosure.

FIG. 13a is a side sectional view of a self-locking fastener 600 engaged with a sleeve portion 602 in accordance with an embodiment of the present invention. In the illustrated embodiment, sleeve portion 602 is a multi-filament structure in the illustrated embodiment. As the surgeon advances filament portion 604 through opening 606 in the sleeve portion 602 in direction 608, the interlock structures 610 deflect inward toward the core 612. Once the surgeon achieves the desired tension on the filament portion 604, the filament portion 604 is displaced slightly in direction 614 until the interlock structures 610 advances into the multi-filament sleeve portion 602. The surgeon can re-tension the filament portion 604 by applying a force in the direction 608. The interlock structures 610 then reset into the multi-filament sleeve portion 602 to form a self-locking mechanical interlock.

In order for the interlock structures 610 to open a sufficient amount to securely engage with the multi-filament sleeve portion 602, clearance 620 is preferably maintained between outer surface 622 of the core 612 and inner surface 624 of the sleeve portion 602. The distance between each interlock structure 610 is a reflection of number of interlock structures per unit length represented as interlock structure density. The interlock structure density may be interdependent on the number of interlocks and filament strength for the application. Increasing the number of interlock structures may produce higher load bearing capacities of the assembly.

The distance of the interlock structure tips 626 to the outer surface 622 can be characterized as interlock structure height 628. Interlock structure height 628 is preferably sufficient so the interlock structures 610 can penetration or otherwise advance into the multi-filament sleeve 602. Adequate clearance 620 between the filament surface 622 and multi-filament sleeve 602 is required for the interlock structures 610 to consistently engage with inner surface 624 of the multi-filament sleeve 602. Consequently, there is an optimum relationship between interlock structure height 628 and clearance 620. In one embodiment, the clearance 620 is between about one-third to about one-half of interlock structure height 628. Thus, the remaining height 628 of the interlock structure 610 is available for penetration and interlocking with the multi-filament sleeve 602. In another embodiment, the clearance 620 is between about 5% to about 95% of the interlock structure height 628, and typically about 30%.

The depth of cut 630 reduces the pull strength of the filament portion 604. To optimize the performance of a self-locking filament 600, it is advantageous to consider varying the interlock structure geometry (cut angle, cut depth, cut length, cut distance, etc.) and/or the spatial arrangement of the interlock structures. Varying these features should not only enhance the tensile strength of a filament, but also should enhance the ability of the interlock structures to form a secure self-locking configuration to hold and maintain wound edges together.

Unlike conventional filaments, which place tensions directly at the knots, the fasteners 600 spread out the tension along length 636 of the sleeve portion 602. Optimizing the disposition and/or the configuration of the interlock structures 610 should therefore further increase the effectiveness of the self-locking function to maximize holding strength and minimize the gap formation along the wound edges. The latter is particularly beneficial for promoting wound healing.

Figure 13B:
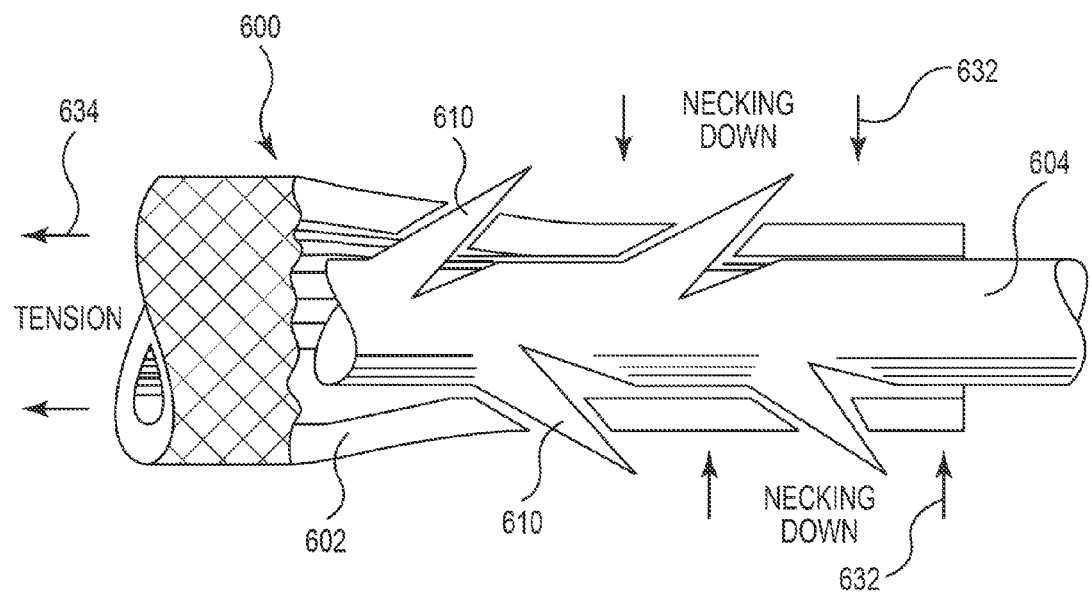
FIG. 13b is a cross-sectional view of an alternate self-locking fastener in accordance with an embodiment of the present invention.

FIG. 13b illustrates an alternate embodiment of the self-locking fastener 600 in which sleeve portion 602 is a textile structure that assumes a necked-down configuration 632 when tension force 634 is applied in accordance with an embodiment of the present invention. Tension force 634 causes sleeve portion 602 to constrict or cinch around filament portion 604. The interlock structures 610 are driven further into the sleeve portion 602, enhancing the mechanical interlock. The tension force 634 is preferably applied by the delivered assembly 570 before releasing the self-locking fastener 600. In one embodiment, the sleeve portion 602 is bonded to the filament portion 604 in the necked-down configuration 632.

Figure 14:
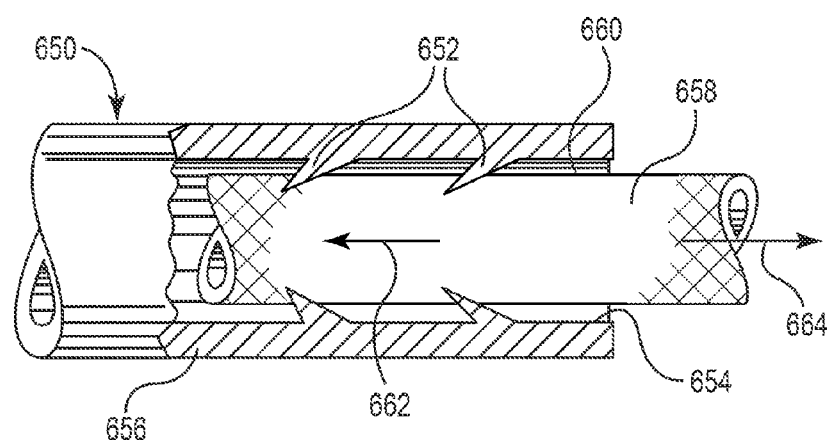
FIG. 14 is a cross-sectional view of an alternate self-locking fastener in a locked configuration in accordance with an embodiment of the present disclosure.

FIG. 14 illustrates an alternate self-locking fastener 650 with interlock structures 652 located on interior surface 654 of sleeve 656. The sleeve 656 can be a molded structure rather than the multi-filament structure discussed above. As the filament portion 658 is advanced through opening 660 in direction 662, the interlock structures 652 deflect. Tension on the filament portion 658 in direction 664, however, is resisted by the interlock structures 652 engaging with the filament portion 658 to form the self-locking configuration. The filament portion 658 is preferably a multi-filament material that permits the interlock structures 652 to penetrate, as illustrated in FIG. 14.

Figure 15:
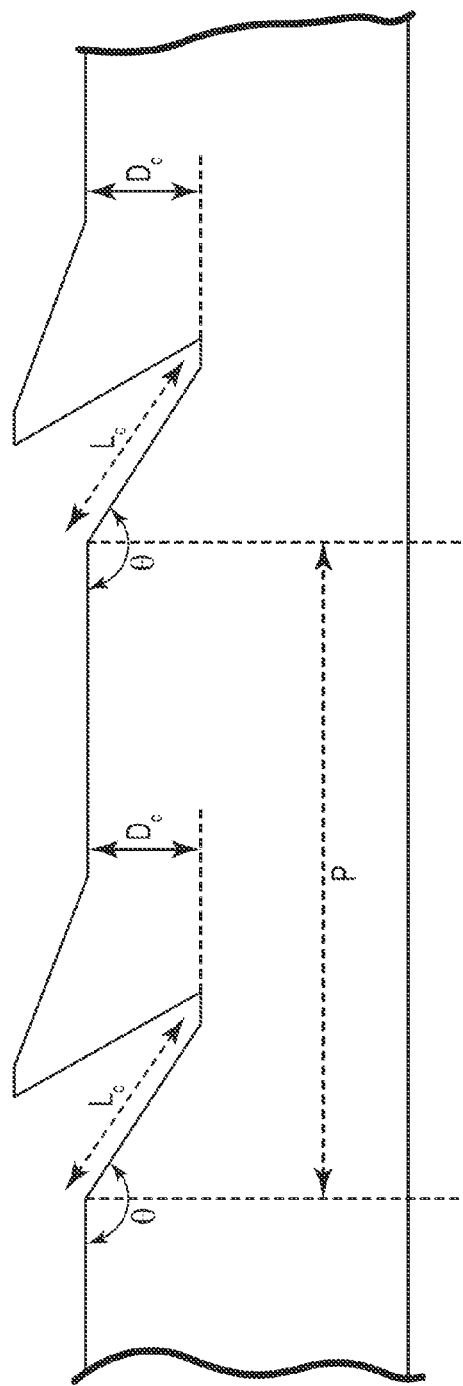
FIG. 15 is a schematic illustration of interlock structures for a self-locking fastener in accordance with an embodiment of the present disclosure.

FIG. 15 is a schematic illustration of the relation between various self-locking parameters, as represented by the following equation.

$$L_c = \frac{D_c}{\sin(180 - \theta)}$$

Where:
$L_c$=Length of the cut
$D_c$=Depth of the cut
P=Distance between the cuts
θ=Cut angle in degrees
P=Interlock structure pitch For example, when the cut angle θ is about 152° and keeping the length of cut $L_c$ to a maximum of about 0.59 millimeters (hereinafter "mm"), the depth of cut $D_c$ is about 0.25 mm. With a cut angle θ of about 172° and the length of cut $L_c$ about 0.34 mm, the depth of cut $D_c$ is about 0.043 mm.

Figure 16:
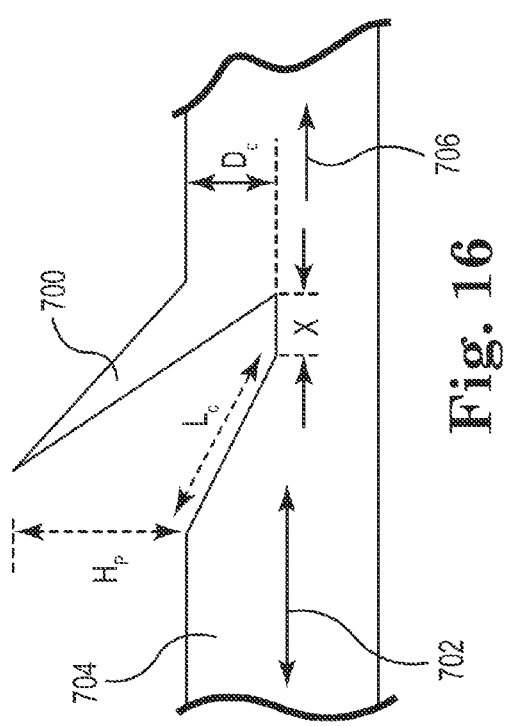
FIG. 16 is a schematic illustration of alternate interlock structures for a self-locking fastener in accordance with an embodiment of the present disclosure.

FIG. 16 illustrates an alternate self-locking fastener 700 in which the cutting blade moves along longitudinal axis 702 of the fiber 704 in direction 706 after reaching the maximum depth of cut $D_c$. The amount of longitudinal motion 706 of the blade is identified as X. A portion of the polymeric material displaced by the longitudinal motion X is added to the interlock structure 700 and increases the overall interlock structure height $H_p$ and the length of the cut $L_c$. In another embodiment, the motion of the cutting blade can be adjusted to vary the length of the cut $L_c$, thus changing the interlock structure height $H_p$, without changing the depth of cut $D_c$.

Figure 17A:
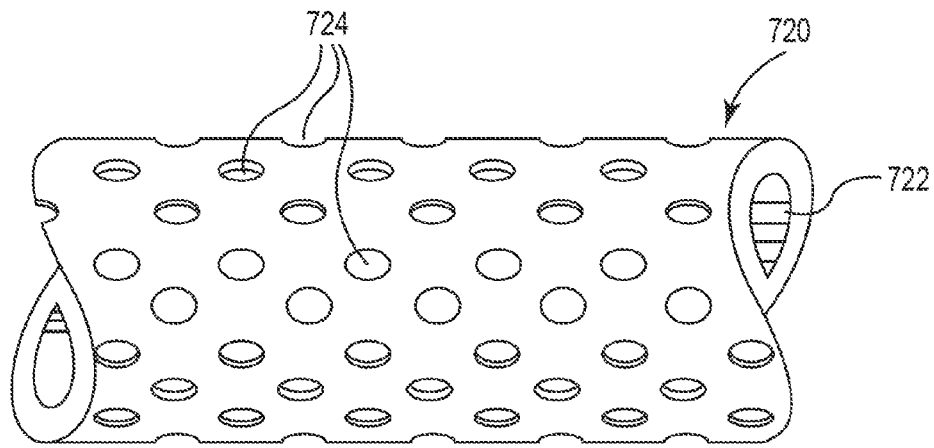
FIGS. 17a and 17b illustrate an alternate self-locking fastener in accordance with an embodiment of the present invention.
Figure 17B:
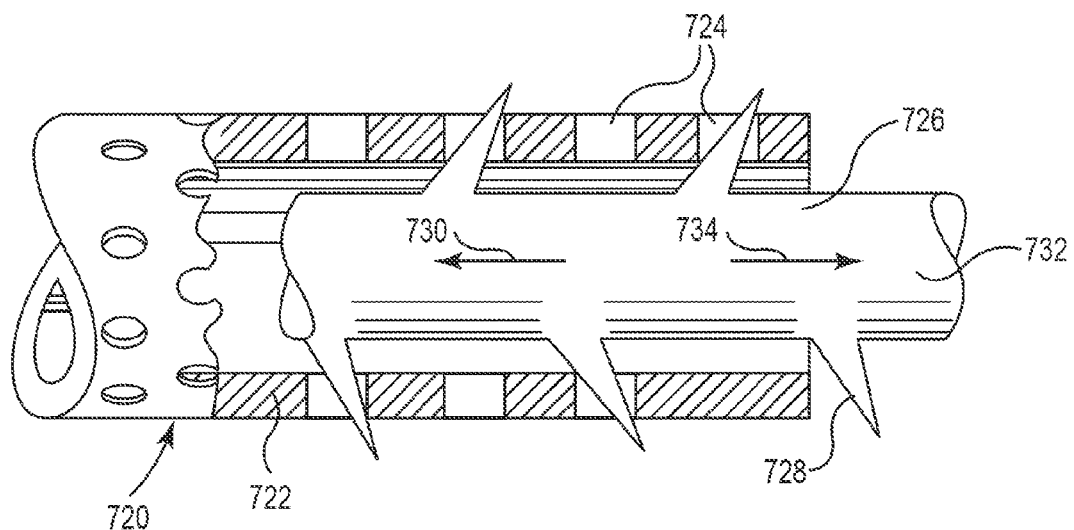

FIGS. 17a and 17b illustrate an alternate self-locking fastener 720 in accordance with an embodiment of the present invention. Sleeve portion 722 is an extruded or molded polymeric structure with a plurality of holes 724. The holes 724 can be made during the extrusion or molding process, or added during a post processing step. Filament portion 726 includes a plurality of interlock structures 728 configured to self-lock with the holes 724.

As best illustrated in FIG. 17b, as the filament portion 726 is advance into opening of the sleeve portion 722 in direction 730, the interlock structures 728 deflect toward the core 732. Once the surgeon achieves the desired tension on the filament portion 726, the filament portion 726 is displaced slightly in direction 734 until some or all of the interlock structures 728 penetrate a hole 724. The surgeon can re-tension the filament portion 726 by applying a force in the direction 730. The interlock structures 728 then reset into a different hole 724 to form a self-locking mechanical interlock.

The filamentous tissue implants of the present disclosure can be used to secure tissue of patient to another structure, such as an artificial implant, a mesh material, or other patient tissue. In preferred embodiments, the filamentous tissue implant has a loop on one end, used to tie a knot, or otherwise cinch, by passing the non-looped end through tissue and other structures, and then through the loop. Cinching can be caused by frictional engagement and/or it may include other fixation means such as a weld (the filamentous implant to itself or another implant), adhesive, interlock structure configuration, webbing, pre-tied knots, connection to a second component; etc.

Systems of the present disclosure may include one or more energy sources such as to cinch a fastener. Heating and welding can be used to provide temporary or permanent fixation of one part of the fastener to the other. Energy sources may also be used to activate grasping mechanisms, position one or more components or assemblies of the delivery tool, activate a tensioning mechanism such as a mechanism used to cinch a fastener, or for other purposes requiring energy.

Numerous kit configurations are also to be considered within the scope of this application. A fixation system is provided with one or more fasteners, and one or more delivery assemblies.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments of the invention. The upper and lower limits of these smaller ranges which may independently be included in the smaller ranges is also encompassed within the embodiments of the invention, subject to any specifically excluded limit in the stated range. Where the stated range includes one or both of the limits, ranges excluding either both of those included limits are also included in the embodiments of the invention.

Unless defined otherwise, all technical and scientific terms used herein have the same meaning as commonly understood by one of ordinary skill in the art to which the embodiments of the present disclosure belong. Although any methods and materials similar or equivalent to those described herein can also be used in the practice or testing of the embodiments of the present disclosure, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the embodiments of the present invention are not entitled to antedate such publication by virtue of prior invention. Further, the dates of publication provided may be different from the actual publication dates which may need to be independently confirmed.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the present disclosure. It should be understood that various features and aspects of the disclosed embodiments can be combined with or substituted for one another in order to form varying modes of the disclosed embodiments of the invention. Thus, it is intended that the scope of at least some of the present invention herein disclosed should not be limited by the particular disclosed embodiments described above.

Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment(s) that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims.

Other embodiments of the disclosure will be apparent to those skilled in the art from consideration of the specification and practice of the disclosure disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth below not be construed as being order-specific unless such order specificity is expressly stated in the claim.

What is claimed is:

1. A method of engaging a tissue fixation system to two or more layers of material, the method comprising the steps of:
   coupling an elongated fastener to an elongated curved needle by positioning the elongated fastener at least partially in an open channel in the elongated curved needle, the elongated curved needle comprising a proximal end attached to a delivery tube and a distal end configured to penetrate the two or more layers of material, the open channel extending from the proximal end to the distal end of the elongated curved needle;
   inserting the distal end of the elongated curved needle and a portion of the elongated fastener though the two or more layers of material;
   advancing a capture needle through the delivery tube and through at least one loop in the elongated fastener;
   mechanically capturing the elongated fastener with the capture needle;
   retracting the capture needle through the delivery tube;
   pulling the elongated fastener through the loop to cinch the elongated fastener to the two or more layers of material; and
   detaching the delivery tube and the elongated curved needle from the elongated fastener.

2. The method of claim 1 wherein positioning the elongated fastener at least partially in the open channel in the elongated curved needle involves positioning the loop near the proximal end of the elongated curved needle.

3. The method of claim 1 wherein positioning the elongated fastener at least partially in the open channel in the elongated curved needle involves positioning the loop near the distal end of the elongated curved needle.

4. The method of claim 1 comprising cinching the elongated fastener by engaging mutually self-locking structures on the elongated fastener as the capture needle is retracted.

5. The method of claim 1 comprising cinching the elongated fastener by engaging interlocking structures at a distal end of the elongated fastener with the loop as the capture needle is retracted.

6. The method of claim 1 wherein the at least one loop comprises a multi-filament sleeve located near a proximal end of the elongated fastener and a distal portion of the elongated fastener comprises a plurality of interlock structures configured to self-lock with the multifilament sleeve, the method comprising:
   positioning the multi-filament sleeve near the proximal end of the elongated curved needle; and
   engaging the interlock structures with the multi-filament sleeve as the capture needle is retracted.

7. The method of claim 6 comprising inserting the interlock structures into the multifilament sleeve in a self-locking configuration.

8. The method of claim 6 comprising wherein the distal portion of the elongated fastener comprises a monofilament, the method comprising forming the interlock structures as a plurality of angled slits in the monofilament.

9. The method of claim 1 wherein the at least one loop comprises a hollow sleeve located at a proximal end of the elongated fastener, the method comprising mechanically coupling a distal end of the elongated fastener with internal structures located in the hollow sleeve.

10. The method of claim 1 wherein the at least one loop comprises a hollow sleeve located at a proximal end of the elongated fastener, the method comprising mechanically coupling interlocking structures on a distal end of the elongated fastener with a hollow sleeve.

11. The method of claim 10 comprising forming openings in the hollow sleeve sized to receive the interlocking structures.

12. The method of claim 1 comprising plastically deforming a distal end of the elongated fastener during the step of retracting the capture needle.

13. The method of claim 1 comprising constructing the elongated fastener from one or more of a bioabsorbable material, a non-bioabsorbable material, or a combination thereof.

14. The method of claim 1 comprising constructing the elongated fastener from a material selected from the group consisting of polylactide, polyglycolide, polysaccharides, proteins, polyesters, polyhydroxyal kanoates, polyalkelene esters, polyamides, polycaprolactone, polyvinyl esters, polyamide esters, polyvinyl alcohols, polyanhydrides, polyolefin, PEEK, PTFE, and their copolymers, modified derivatives of caprolactone polymers, polytrimethylene carbonate, polyacrylates, polyethylene glycol, hydrogels, photo-curable hydrogels, terminal diols, metal fibers, and combinations thereof.

15. The method of claim 1 comprising transitioning jaws on the capture needle from an open position to a closed position to capture the elongated fastener.

16. The method of claim 1 comprising bonding a distal end of the elongated fastener to the loop.

17. A method of engaging a tissue fixation system to two or more layers of material, the method comprising the steps of:
- positioning an elongated fastener at least partially in an open channel in an elongated curved needle, the elongated curved needle comprising a proximal end attached to a delivery tube and a distal end configured to penetrate the two or more layers of material, the open channel extending from the proximal end to the distal end of the elongated curved needle;
- inserting the distal end of the elongated curved needle and a portion of the elongated fastener though the two or more layers of material;
- advancing a capture needle through the delivery tube and through at least one loop in the elongated fastener;
- mechanically capturing the elongated fastener with the capture needle at a location near the distal end of the elongated curved needle;
- retracting the capture needle through the deliver tube and pulling the elongated fastener through the loop to cinch the elongated fastener to the two or more layers of material; and
- detaching the delivery tube and the elongated curved needle from the elongated fastener.

18. The method of claim 17 comprising positioning the loop near the proximal end of the elongated curved needle.

19. The method of claim 17 comprising positioning the loop near the distal end of the elongated curved needle.

* * * * *